(12) United States Patent
Pae et al.

(10) Patent No.: US 8,232,279 B2
(45) Date of Patent: Jul. 31, 2012

(54) PYRAZOLOPYRIMIDINE DERIVATIVES HAVING BIOLOGICAL ACTIVITY ON SEROTONIN RECEPTOR 5-HT2C

(75) Inventors: Ae Nim Pae, Seoul (KR); Hyunah Choo, Seoul (KR); Yong Seo Cho, Seoul (KR); Ahmed Asif, Seoul (KR); Woo-Kyu Park, Cheongju-si (KR)

(73) Assignee: Korea Institute of Science and Technology, Seoul (KR)

( * ) Notice: Subject to any disclaimer, the term of this patent is extended or adjusted under 35 U.S.C. 154(b) by 150 days.

(21) Appl. No.: 12/575,235

(22) Filed: Oct. 7, 2009

(65) Prior Publication Data
US 2010/0298563 A1 Nov. 25, 2010

(30) Foreign Application Priority Data
May 19, 2009 (KR) .................. 10-2009-0043728

(51) Int. Cl.
*A01N 43/90* (2006.01)
*A61K 31/519* (2006.01)
*C07D 487/00* (2006.01)

(52) U.S. Cl. .................... 514/262.1; 544/262
(58) Field of Classification Search .................... None
See application file for complete search history.

(56) References Cited

FOREIGN PATENT DOCUMENTS
EP 2025678 * 2/2009

OTHER PUBLICATIONS
European Journal of Medicinal Chemistry (2003), 38(5), 525-532.*

\* cited by examiner

*Primary Examiner* — Jeffrey Murray
(74) *Attorney, Agent, or Firm* — Frommer Lawrence & Haug LLP; Ronald R Santucci

(57) ABSTRACT

The present invention relates to a novel medicinal use of pyrazolopyrimidine compounds having superior effect as serotonin 5-$HT_{2C}$ receptor ligand thus being useful for the prevention and treatment of central nervous system (CNS) diseases. Accordingly, the pharmaceutical composition comprising pyrazolopyrimidine compounds and their pharmaceutically acceptable salts as active ingredients are useful for the prevention and treatment of serotonin 5-$HT_{2C}$-related central nervous system diseases such as obesity, depression, anxiety and withdrawal symptoms due to drug abuse.

9 Claims, No Drawings

PYRAZOLOPYRIMIDINE DERIVATIVES HAVING BIOLOGICAL ACTIVITY ON SEROTONIN RECEPTOR 5-HT2C

CROSS-REFERENCE TO RELATED APPLICATION

This application claims under 35 U.S.C. §119(a) the benefit of Korean Patent Application No. 10-2009-0043728 filed May 19, 2009, the entire contents of which are incorporated herein by reference.

BACKGROUND (a) Technical Field

The present invention relates to a novel medicinal use of pyrazolopyrimidine compounds having superior effect as serotonin 5-HT$_{2C}$ receptor ligand thus being useful for the prevention and treatment of central nervous system (CNS) diseases.

(b) Background Art

Receptors of serotonin, a neurotransmitter, are known to be involved in various mental disorders (e.g., depression, aggressiveness, seizure, compulsive neurosis, psychosis, schizophrenia and suicidal tendency), neurodegenerative disorders (e.g., Alzheimer's disease, Parkinson's disease and Huntington's chorea), sitophobia, bulimia, alcoholism-related disorders, cerebral vascular accidents and migraine [Meltzer, Neuropsychopharmacology, 21:106 S-115S (1999); Barnes & Sharp, Neuropharmacology, 38:1083-1152 (1999); Glennon, Neurosci. Biobehavioral Rev., 14:35 (1990)].

Serotonin 5-hydroxytryptamine (5-HT) receptors are widely distributed throughout the bodies of humans and animals and play an important role in physiological and behavioral functions. So far, about 15 genetically different 5-HT receptor subtypes have been cloned. Each subtype exhibits unique distribution and shows various preference and relationships for different ligands. Recently, 5-HT receptor subtypes have been shown to be related to the causes of diseases such as hypertension, thrombus, migraine, vasospasm, ischemia, depression, anxiety, psychosis, schizophrenia, sleep disorder and appetite disorder. Among serotonin 5-HT$_2$ family, 5-HT$_{2A}$ and 5-HT$_{2B}$ receptors are abundant in peripheral nervous system, whereas serotonin 5-HT$_{2C}$ receptors are abundant in central nervous system, especially in brain. Therefore, it has been expected that a novel ligand acting effectively on serotonin 5-HT$_{2C}$ would be useful as a new drug for the treatment of CNS diseases such as obesity, depression, anxiety, and withdrawal symptoms due to drug abuse.

WO2009/023978 confirms the inhibitory activity of pyrazolo[3,4-D]pyrimidine against EphB4 receptor tyrosine kinase, and based on this, it teaches that the compound is effective as a therapeutic agent for the treatment of proliferative diseases associated with the protein kinase activity. However, there has been no report yet that discloses the superior activity of pyrazolopyrimidine as a ligand acting on serotonin 5-HT$_{2C}$ to show its effectiveness in the prevention and treatment of CNS diseases such as withdrawal symptoms due to obesity, depression, anxiety, and drug abuse.

SUMMARY

An object of the present invention is to provide a pharmaceutical composition comprising a pyrazolopyrimidine compound, having superior effect as serotonin 5-HT$_{2C}$ receptor ligand, or its pharmaceutically acceptable salt as active ingredient for the prevention and treatment of CNS diseases.

More specifically, the object of the present invention is to provide a pharmaceutical composition comprising a pyrazolopyrimidine compound or its pharmaceutically acceptable salt as active ingredient for the prevention and treatment of obesity, depression, anxiety and withdrawal symptoms due to drug abuse.

Accordingly, the present invention provides a pharmaceutical composition comprising a pyrazolopyrimidine compound represented by the following formula 1 or its pharmaceutically acceptable salt, which is related to serotonin 5-HT$_{2C}$ receptors, as active ingredient for the prevention and treatment of CNS diseases.

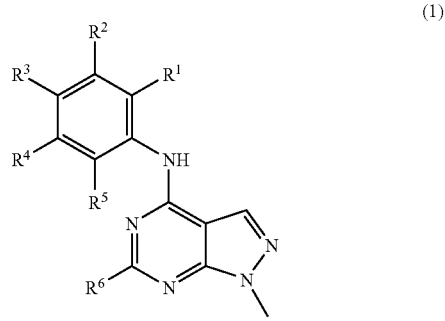

(1)

In the above formula 1, $R^1$, $R^2$, $R^3$, $R^4$, and $R^5$ are independently H, halogen, $C_1$-$C_6$ alkyl, $C_1$-$C_6$ alkoxy; and $R^6$ is selected from the group consisting of $C_1$-$C_6$ alkylamino, di($C_1$-$C_6$ alkyl)amino, $C_1$-$C_6$ hydroxyalkylamino, $C_1$-$C_6$ alkoxy$C_1$-$C_6$ alkylamino, $C_2$-$C_6$ alkenylamino, $C_3$-$C_6$ cycloalkylamino, substituted or unsubstituted benzylamino, morpholino $C_1$-$C_6$ alkylamino, morpholinyl, substituted or unsubstituted piperidinyl, substituted or unsubstituted piperazinyl; and the above substituted benzyl, piperidinyl, piperazinyl represent benzyl, piperidinyl, piperazinyl, or piperazinyl with 1-3 substituents selected from the group consisting of $C_1$-$C_6$ alkyl, hydroxy $C_1$-$C_6$ alkyl, phenyl, halophenyl, $C_1$-$C_6$ alkoxyphenyl, benzyl, and halobenzyl.

DESCRIPTION OF THE INVENTION

The pyrazolopyrimidine compound of the above formula 1 is a known compound. The inventors of the present invention firstly discovered that the above compound has superior activity as a ligand to serotonin 5-HT$_{2C}$ receptors and therefore provides a novel medicinal use of the compound.

Since the above pyrazolopyrimidine compound of the above formula 1 can be easily synthesized by a skilled person in the art using a known method, the present invention does not claim or limit the method of its preparation.

In the pyrazolopyrimidine of the above formula 1, being added as an active ingredient of the pharmaceutical composition of the present invention, more preferably, $R^1$, $R^2$, $R^3$, $R^4$, and $R^5$ are independently H, F, Cl, methyl, ethyl, methoxy, or ethoxy; and $R^6$ is selected from the group consisting of methyl amino, ethyl amino, propylamino, butylamino, cyclopentylamino, cyclohexylamino, dimethyl amino, diethyl amino, (hydroxymethyl)amino, (hydroxyethyl)amino, (hydroxypropyl)amino, (methoxymethyl)amino, (methoxyethyl)amino, (methoxypropyl)amino, (ethoxymethyl)amino, (ethoxyethyl)amino, allylamino, benzylamino, (methylbenzyl)amino, (morpholinomethyl)amino, (morpholinoethyl)

amino, morpholinyl, piperidine, methylpiperidine, dimethylpiperidine, piperazine, methylpiperazine, hydroxymethylpiperazine, hydroxyethylpiperazine, phenylpiperazine, (halophenyl)piperazine, (methoxyphenyl)piperazine, and benzylpiperazine.

In the pyrazolopyrimidine of the above formula 1, being added as an active ingredient of the pharmaceutical composition of the present invention, most preferably, $R^1$, $R^2$, $R^3$, $R^4$, and $R^5$ are independently H, F, methyl, or methoxy; and $R^6$ is selected from the group consisting of methyl amino, ethyl amino, propylamino, cyclopentylamino, cyclohexylamino, dimethyl amino, diethyl amino, (hydroxypropyl)amino, (methoxyethyl)amino, (methoxypropyl)amino, allylamino, benzylamino, (4-methylbenzyl)amino, (morpholinoethyl)amino, morpholinyl, piperidine, 4-methylpiperidine, 3,5-dimethylpiperidine, piperazine, 4-methylpiperazine, 4-hydroxyethylpiperazine, 4-phenylpiperazine, 4-(p-fluorophenyl)piperazine, 4-(2-methoxyphenyl)piperazine, and 4-benzylpiperazine.

The pyrazolopyrimidine compounds of the present invention can be exemplified as follows.

Compound No. 1: $N^6$-ethyl-1-methyl-$N^4$-phenyl-1H-pyrazolo[3,4-d]pyrimidine-4,6-diamine
Compound No. 2: 1-methyl-$N^4$-phenyl-$N^6$-propyl-1H-pyrazolo[3,4-d]pyrimidine-4,6-diamine
Compound No. 3: 1-methyl-6-(4-methylpiperazine-1-yl)-N-phenyl-1H-pyrazolo[3,4-d]pyrimidine-4-amine
Compound No. 4: $N^4$-(3,4-dimethylphenyl)-$N^6$,$N^6$-diethyl-1-methyl-1H-pyrazolo[3,4-d]pyrimidine-4,6-diamine
Compound No. 5: $N^4$-(4-chlorophenyl)-$N^6$,$N^6$-diethyl-1-methyl-1H-pyrazolo[3,4-d]pyrimidine-4,6-diamine
Compound No. 6: $N^6$-(4-chlorophenyl)-1-methyl-6-(4-methylpiperazine-1-yl)-1H-pyrazolo[3,4-d]pyrimidine-4-amine
Compound No. 7: $N^6$,$N^6$-diethyl-1-methyl-$N^4$-o-tolyl-1H-pyrazolo[3,4-d]pyrimidine-4,6-diamine
Compound No. 8: $N^4$-(4-fluorophenyl)-$N^6$,1-dimethyl-1H-pyrazolo[3,4-d]pyrimidine-4,6-diamine
Compound No. 9: $N^6$-ethyl-$N^4$-(4-fluorophenyl)-1-methyl-1H-pyrazolo[3,4-d]pyrimidine-4,6-diamine
Compound No. 10: 3-(4-(4-fluorophenyl amino)-1-methyl-1H-pyrazolo[3,4-d]pyrimidine-6-yl amino)propane-1-ol
Compound No. 11: $N^4$-(4-fluorophenyl)-$N^6$-(2-methoxyethyl)-1-methyl-1H-pyrazolo[3,4-d]pyrimidine-4,6-diamine
Compound No. 12: $N^4$-(4-fluorophenyl)-$N^6$-(3-methoxypropyl)-1-methyl-1H-pyrazolo[3,4-d]pyrimidine-4,6-diamine
Compound No. 13: $N^6$-allyl-$N^4$-(4-fluorophenyl)-1-methyl-1H-pyrazolo[3,4-d]pyrimidine-4,6-diamine
Compound No. 14: $N^6$-cyclohexyl-$N^4$-(4-fluorophenyl)-1-methyl-1H-pyrazolo[3,4-d]pyrimidine-4,6-diamine
Compound No. 15: $N^6$-cyclopentyl-$N^4$-(4-fluorophenyl)-1-methyl-1H-pyrazolo[3,4-d]pyrimidine-4,6-diamine
Compound No. 16: $N^6$-benzyl-N4-(4-fluorophenyl)-1-methyl-1H-pyrazolo[3,4-d]pyrimidine-4,6-diamine
Compound No. 17: $N^4$-(4-fluorophenyl)-1-methyl-$N^6$-(4-methylbenzyl)-1H-pyrazolo[3,4-d]pyrimidine-4,6-diamine
Compound No. 18: $N^4$-(4-fluorophenyl)-1-methyl-$N^6$-(2-morpholinoethyl)-1H-pyrazolo[3,4-d]pyrimidine-4,6-diamine
Compound No. 19: $N^4$-(4-fluorophenyl)-$N^6$,$N^6$,1-trimethyl-1H-pyrazolo[3,4-d]pyrimidine-4,6-diamine
Compound No. 20: $N^6$,$N^6$-diethyl-$N^4$-(4-fluorophenyl)-1-methyl-1H-pyrazolo[3,4-d]pyrimidine-4,6-diamine
Compound No. 21: N-(4-fluorophenyl)-1-methyl-6-morpholino-1H-pyrazolo[3,4-d]pyrimidine-4-amine
Compound No. 22: N-(4-fluorophenyl)-1-methyl-6-(piperidine-1-yl)-1H-pyrazolo[3,4-d]pyrimidine-4-amine
Compound No. 23: 6-(3,5-dimethylpiperidine-1-yl)-N-(4-fluorophenyl)-1-methyl-1H-pyrazolo[3,4-d]pyrimidine-4-amine
Compound No. 24: N-(4-fluorophenyl)-1-methyl-6-(4-methylpiperidine-1-yl)-1H-pyrazolo[3,4-d]pyrimidine-4-amine
Compound No. 25: N-(4-fluorophenyl)-1-methyl-6-(4-methylpiperazine-1-yl)-1H-pyrazolo[3,4-d]pyrimidine-4-amine
Compound No. 26: 2-(4-(4-(4-fluorophenyl amino)-1-methyl-1H-pyrazolo[3,4-d]pyrimidine-6-yl)piperazine-1-yl)ethanol
Compound No. 27: 6-(4-benzylpiperazine-1-yl)-N-(4-fluorophenyl)-1-methyl-1H-pyrazolo[3,4-d]pyrimidine-4-amine
Compound No. 28: N-(4-fluorophenyl)-1-methyl-6-(4-phenylpiperazine-1-yl)-1H-pyrazolo[3,4-d]pyrimidine-4-amine
Compound No. 29: N-(4-fluorophenyl)-6-(4-(4-fluorophenyl)piperazine-1-yl)-1-methyl-1H-pyrazolo[3,4-d]pyrimidine-4-amine
Compound No. 30: N-(4-fluorophenyl)-6-(4-(2-methoxyphenyl)piperazine-1-yl)-1-methyl-1H-pyrazolo[3,4-d]pyrimidine-4-amine
Compound No. 31: $N^6$,$N^6$-diethyl-$N^4$-(3-methoxyphenyl)-1-methyl-1H-pyrazolo[3,4-d]pyrimidine-4,6-diamine
Compound No. 32: N-(3-methoxyphenyl)-1-methyl-6-(4-methylpiperazine-1-yl)-1H-pyrazolo[3,4-d]pyrimidine-4-amine
Compound No. 33: 6-(4-(4-fluorophenyl)piperazine-1-yl)-N-(3-methoxyphenyl)-1-methyl-1H-pyrazolo[3,4-d]pyrimidine-4-amine
Compound No. 34: 6-(4-(4-fluorophenyl)piperazine-1-yl)-N-(4-methoxyphenyl)-1-methyl-1H-pyrazolo[3,4-d]pyrimidine-4-amine
Compound No. 35: N-(4-fluorophenyl)-1-methyl-6-(4-methylpiperazine-1-yl)-1H-pyrazolo[3,4-d]pyrimidine-4-amine.

In the present invention, the pharmaceutically acceptable salts can be prepared by a method commonly used by those skilled in the art. For example, it may be a salt with an inorganic acid such as hydrochloric acid, bromic acid, sulfuric acid, sodium bisulfate, phosphoric acid, nitric acid, carbonic acid, etc.; a salt with an organic acid such as such as formic acid, acetic acid, propionic acid, oxalic acid, succinic acid, benzoic acid, citric acid, maleic acid, malonic acid, tartaric acid, gluconic acid, lactic acid, gestisic acid, fumaric acid, lactobionic acid, salicylic acid, trifluoroacetic acid, acetylsalicylic acid (aspirin), etc.; a salt with an amino acid such as glycine, alanine, valine, isoleucine, serine, cysteine, cystine, asparaginic acid, glutamine, lysine, arginine, tyrosine, proline, etc.; a salt with a sulfonic acid such as methanesulfonic acid, ethanesulfonic acid, benzenesulfonic acid, toluenesulfonic acid, etc.; a metal salt obtained from a reaction with an alkali metal such as sodium, potassium, etc.; or a salt with an ammonium ion.

Further, in addition to the compound represented by the formula (1) or a pharmaceutically acceptable salt thereof, the pharmaceutical composition of the present invention may comprise a commonly used nontoxic pharmaceutically acceptable carrier, strengthener, excipient, etc., to be prepared into oral or parenteral preparation forms commonly used in pharmaceutical fields, for example, tablets, capsules, troches, liquid, suspensions, etc., for the prevention and treatment of tumors.

The excipient that may be used in the pharmaceutical composition of the present invention includes a sweetener, a binder, a dissolver, a dissolution aid, a wetting agent, an emulsifier, an isotonizer, an adsorbent, a disintegrator, an antioxidant, an antiseptic, a lubricant, a filler, an aromatic, etc. For example, lactose, dextrose, sucrose, mannitol, sorbitol, cellulose, glycine, silica, talc, stearic acid, sterine, magnesium stearate, magnesium aluminum silicate, starch, gelatin, tragacanth gum, alginic acid, sodium alginate, methylcellulose, sodium carboxymethyl cellulose, agar, water, ethanol, polyethylene glycol, polyvinyl pyrrolidone, sodium chloride, calcium chloride, orange essence, strawberry essence, vanilla flavor, etc.

The administration dosage of the compound represented by the formula (1) may vary depending on the patient's age, body weight, sex, administration route, physical conditions and severity of disease. In general, a daily dosage for an adult patient weighing 70 kg is 0.01 mg to 5000 mg. The administration may be given once to several times a day at predetermined intervals as instructed by a doctor or pharmacist.

Hereunder is given a more detailed description of the present invention with reference to the following examples. However, they should not be construed as limiting the scope of the present invention.

[Biological Assay]

[$^3$H]Mesulergine Binding to Serotonin 5-HT$_{2C}$ Receptor

Frozen membranes from stable CHO—K1 cell line expressing the human recombinant 5-HT$_{2C}$ receptor were used. For the binding assay, [$^3$H]Mesulergine (1 nM), receptor membrane (4 ug/well) and test compounds were added into 50 mM Tris-HCl (pH 7.7) buffer containing 0.1% ascorbic acid and 10 uM pargyline. Nonspecific binding was determined using 0.5 uM mianserin. The incubations were performed for 30 min at 37° C., and these were terminated by rapid filtration through Whatman GF/C glass fiber filters presoaked in 1% BSA. Then, the resultant was washed with cold 50 mM Tris-HCl buffer. The filter was covered with MeltiLex, sealed in a sample bag followed by drying in the microwave oven, and counted by MicroBeta Plus (Wallac, Finland). Nonspecific binding was determined in the presence of mianserin (0.5 uM). Competition binding studies were carried out with 7-8 varied concentrations of the test compounds run in duplicate tubes, and isotherms from three assays were calculated by computerized nonlinear regression analysis (GraphPad Prism Program, San Diego, USA) to yield IC$_{50}$ values (Table 1).

TABLE 1

| Test Compound | Affinity for 5-HT$_{2C}$ receptor (IC$_{50}$, nM) |
| --- | --- |
| Comp. 1 | >10000 |
| Comp. 2 | >10000 |
| Comp. 3 | 86.9 |
| Comp. 4 | 8491 |
| Comp. 5 | 991 |
| Comp. 6 | 29.4 |
| Comp. 7 | 242 |
| Comp. 8 | 7787 |
| Comp. 9 | >1000 |
| Comp. 10 | >1000 |
| Comp. 11 | >1000 |
| Comp. 12 | >1000 |
| Comp. 13 | >1000 |
| Comp. 14 | 5713 |

TABLE 1-continued

| Test Compound | Affinity for 5-HT$_{2C}$ receptor (IC$_{50}$, nM) |
| --- | --- |
| Comp. 15 | >1000 |
| Comp. 16 | 2588 |
| Comp. 17 | 5833 |
| Comp. 18 | >1000 |
| Comp. 19 | 4027 |
| Comp. 20 | 3306 |
| Comp. 21 | 2071 |
| Comp. 22 | 1300 |
| Comp. 23 | 3817 |
| Comp. 24 | 1500 |
| Comp. 25 | 85.8 |
| Comp. 26 | 494 |
| Comp. 27 | 836 |
| Comp. 28 | 416 |
| Comp. 29 | 148 |
| Comp. 30 | 1725 |
| Comp. 31 | 5422 |
| Comp. 32 | 7.8 |
| Comp. 33 | 1085 |
| Comp. 34 | 1179 |
| Comp. 35 | 20.1 |

The compounds represented by the above formula 1 may be prepared in various forms as necessary. The following preparation examples only illustrate a few formulations comprising the compounds represented by the above formula 1 and shall not be construed as limiting the scope of the present invention.

PREPARATION EXAMPLES

Preparation 1

Tablets (Direct Pressure)

5.0 mg of active ingredient was sieved, mixed with 14.1 mg of lactose, 0.8 mg of crospovidone USNF, and 0.1 mg of magnesium stearate. Then, the mixture was pressured to obtain tablets.

Preparation 2

Tablets (Wet Granulation)

5.0 mg of active ingredient was sieved, mixed with 16.0 mg of lactose, and 4.0 mg of starch, and then further added with an adequate amount of a solution, which was prepared by dissolving 0.3 mg of Polysorbate 80 in distilled water, and the mixture was atomized. After drying, the atomized particles were sieved, added with 2.7 mg of colloidal silicon dioxide and 2.0 mg of magnesium stearate, and then pressed to obtain tablets.

Preparation 3

Powders and Capsules 5.0 mg of active ingredient was sieved, mixed with 14.8 mg of lactose, and 10.0 mg of polyvinyl pyrrolidone, 0.2 mg of magnesium stearate. The mixture was filled into a No. 5 hard gelatin capsule by using a suitable apparatus.

Preparation 4

Injections 100 mg of active ingredient was added along with 180 mg of mannitol, 26 mg of $Na_2HPO_4.12H_2O$ and 2974 mg of distilled water to prepare an injection.

INDUSTRIAL APPLICABILITY

The pharmaceutical composition of the present invention has superior binding affinity for and is thus expected to be used as a therapeutic agent for the prevention and treatment of CNS diseases such as obesity, depression, anxiety, and withdrawal symptoms due to drug abuse.

The invention claimed is:

1. A pharmaceutical composition comprising a pyrazolopyrimidine compound or a pharmaceutically acceptable salt of the formula 1 and a pharmaceutically acceptable carrier for the prevention and treatment of serotonin 5-$HT_{2C}$-related central nervous system diseases selected from the group consisting of obesity, depression, anxiety and withdrawal symptoms due to drug abuse:

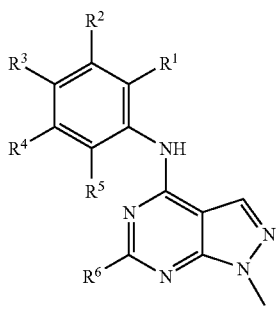

[1]

wherein $R^1$, $R^2$, $R^3$, $R^4$, and $R^5$ independently represent H, halogen, $C_1$-$C_6$ alkyl, $C_1$-$C_6$ alkoxy; and $R^6$ is selected from the group consisting of $C_1$-$C_6$ alkylamino, di($C_1$-$C_6$ alkyl) amino, $C_1$-$C_6$ hydroxyalkylamino, $C_1$-$C_6$ alkoxy$C_1$-$C_6$ alkylamino, $C_2$-$C_6$ alkenylamino, $C_3$-$C_6$ cycloalkylamino, substituted or unsubstituted benzylamino, morpholino $C_1$-$C_6$ alkylamino, morpholinyl, substituted or unsubstituted piperidinyl, substituted or unsubstituted piperazinyl; wherein the above substituted benzyl, piperidinyl, or piperazinyl represents benzyl, piperidinyl, or piperazinyl substituted with 1-3 substituents selected from the group consisting of $C_1$-$C_6$ alkyl, hydroxy $C_1$-$C_6$ alkyl, phenyl, halophenyl, $C_1$-$C_6$ alkoxyphenyl, benzyl, and halobenzyl.

2. The pharmaceutical composition according to claim 1, wherein in the formula 1, $R^1$, $R^2$, $R^3$, $R^4$, and $R^5$ individually represent H, F, Cl, methyl, ethyl, methoxy, or ethoxy; and $R^6$ is selected from the group consisting of methyl amino, ethyl amino, propylamino, butylamino, cyclopentylamino, cyclohexylamino, dimethyl amino, (hydroxymethyl)amino, (hydroxypropyl)amino, (methoxymethyl)amino, (methoxyethyl)amino, (methoxypropyl)amino, (ethoxymethyl)amino, (ethoxyethyl)amino, allylamino, benzylamino, (methylbenzyl)amino, (morpholinomethyl)amino, (morpholinoethyl) amino, morpholinyl, piperidine, methylpiperidine, dimethylpiperidine, piperazine, methylpiperazine, hydroxymethylpiperazine, hydroxyethylpiperazine, phenylpiperazine, (halophenyl)piperazine, (methoxyphenyl)piperazine, and benzylpiperazine.

3. The pharmaceutical composition according to claim 1, wherein the pyrazolopyrimidine compound represented by the above formula 1 is selected from the group consisting of $N^6$-ethyl-1-methyl-$N^4$-phenyl-1H-pyrazolo[3,4-d]pyrimidine-4,6-diamine; 1-methyl-$N^4$-phenyl-$N^6$-propyl-1H-pyrazolo[3,4-d]pyrimidine-4,6-diamine; 1-methyl-6-(4-methylpiperazine-1-yl)-N-phenyl-1H-pyrazolo[3,4-d]pyrimidine-4-amine; $N^4$-(3,4-dimethylphenyl)-$N^6$,$N^6$-diethyl-1-methyl-1H-pyrazolo[3,4-d]pyrimidine-4,6-diamine; $N^4$-(4-chlorophenyl)-$N^6$,$N^6$-diethyl-1-methyl-1H-pyrazolo[3,4-d]pyrimidine-4,6-diamine; $N^6$-(4-chlorophenyl)-1-methyl-6-(4-methylpiperazine-1-yl)-1H-pyrazolo[3,4-d]pyrimidine-4-amine; $N^6$,$N^6$-diethyl-1-methyl-$N^4$-o-tolyl-1H-pyrazolo[3,4-d]pyrimidine-4,6-diamine; $N^4$-(4-fluorophenyl)-$N^6$,1-dimethyl-1H-pyrazolo[3,4-d]pyrimidine-4,6-diamine; $N^6$-ethyl-$N^4$-(4-fluorophenyl)-1-methyl-1H-pyrazolo[3,4-d]pyrimidine-4,6-diamine; $N^4$-(4-fluorophenyl)-$N^6$-(2-methoxyethyl)-1-methyl-1H-pyrazolo[3,4-d]pyrimidine-4,6-diamine; $N^4$-(4-fluorophenyl)-$N^6$-(3-methoxypropyl)-1-methyl-1H-pyrazolo[3,4-d]pyrimidine-4,6-diamine; $N^6$-allyl-$N^4$-(4-fluorophenyl)-1-methyl-1H-pyrazolo[3,4-d]pyrimidine-4,6-diamine; $N^6$-cyclohexyl-$N^4$-(4-fluorophenyl)-1-methyl-1H-pyrazolo[3,4-d]pyrimidine-4,6-diamine; $N^6$-cyclopentyl-$N^4$-(4-fluorophenyl)-1-methyl-1H-pyrazolo[3,4-d]pyrimidine-4,6-diamine; $N^6$-benzyl-$N^4$-(4-fluorophenyl)-1-methyl-1H-pyrazolo[3,4-d]pyrimidine-4,6-diamine; $N^4$-(4-fluorophenyl)-1-methyl-$N^6$-(4-methylbenzyl)-1H-pyrazolo[3,4-d]pyrimidine-4,6-diamine; $N^4$-(4-fluorophenyl)-1-methyl-$N^6$-(2-morpholinoethyl)-1H-pyrazolo[3,4-d]pyrimidine-4,6-diamine; $N^4$-(4-fluorophenyl)-$N^6$,$N^6$,1-trimethyl-1H-pyrazolo[3,4-d]pyrimidine-4,6-diamine; $N^6$,$N^6$-diethyl-$N^4$-(4-fluorophenyl)-1-methyl-1H-pyrazolo[3,4-d]pyrimidine-4,6-diamine; N-(4-fluorophenyl)-1-methyl-6-morpholino-1H-pyrazolo[3,4-d]pyrimidine-4-amine; N-(4-fluorophenyl)-1-methyl-6-(piperidine-1-yl)-1H-pyrazolo[3,4-d]pyrimidine-4-amine; 6-(3,5-dimethylpiperidine-1-yl)-N-(4-fluorophenyl)-1-methyl-1H-pyrazolo[3,4-d]pyrimidine-4-amine; N-(4-fluorophenyl)-1-methyl-6-(4-methylpiperidine-1-yl)-1H-pyrazolo[3,4-d]pyrimidine-4-amine; N-(4-fluorophenyl)-1-methyl-6-(4-methylpiperazine-1-yl)-1H-pyrazolo[3,4-d]pyrimidine-4-amine; 2-(4-(4-(4-fluorophenyl amino)-1-methyl-1H-pyrazolo[3,4-d]pyrimidine-6-yl)piperazine-1-yl)ethanol; 6-(4-benzylpiperazine-1-yl)-N-(4-fluorophenyl)-1-methyl-1H-pyrazolo[3,4-d]pyrimidine-4-amine; N-(4-fluorophenyl)-1-methyl-6-(4-phenylpiperazine-1-yl)-1H-pyrazolo[3,4-d]pyrimidine-4-amine; N-(4-fluorophenyl)-6-(4-(4-fluorophenyl)piperazine-1-yl)-1-methyl-1H-pyrazolo[3,4-d]pyrimidine-4-amine; N-(4-fluorophenyl)-6-(4-(2-methoxyphenyl)piperazine-1-yl)-1-methyl-1H-pyrazolo[3,4-d]pyrimidine-4-amine; N-(3-methoxyphenyl)-1-methyl-6-(4-methylpiperazine-1-yl)-1H-pyrazolo[3,4-d]pyrimidine-4-amine; 6-(4-(4-fluorophenyl)piperazine-1-yl)-N-(3-methoxyphenyl)-1-methyl-1H-pyrazolo[3,4-d]pyrimidine-4-amine; 6-(4-(4-fluorophenyl)piperazine-1-yl)-N-(4-methoxyphenyl)-1-methyl-1H-pyrazolo[3,4-d]pyrimidine-4-amine; and N-(4-fluorophenyl)-1-methyl-6-(4-methylpiperazine-1-yl)-1H-pyrazolo[3,4-d]pyrimidine-4-amine.

4. The pharmaceutical composition of claim 1, wherein $R^1$, $R^2$, $R^3$, $R^4$, and $R^5$ independently represent H, halogen, $C_1$-$C_6$ alkyl, $C_1$-$C_6$ alkoxy; and $R^6$ is selected from the group consisting of $C_1$-$C_6$ alkylamino, $C_1$-$C_6$ alkoxy$C_1$-$C_6$ alkylamino, $C_2$-$C_6$ alkenylamino, $C_3$-$C_6$ cycloalkylamino, substituted or unsubstituted benzylamino, morpholino $C_1$-$C_6$ alkylamino, morpholinyl, substituted or unsubstituted piperidinyl, substituted or unsubstituted piperazinyl; wherein the above substituted benzyl, piperidinyl, or piperazinyl represents benzyl, piperidinyl, or piperazinyl substituted with 1-3 substituents selected from the group consisting of $C_1$-$C_6$ alkyl, hydroxy $C_1$-$C_6$ alkyl, phenyl, halophenyl, $C_1$-$C_6$ alkoxyphenyl, benzyl, and halobenzyl.

5. The pharmaceutical composition according to claim 1, wherein in the formula 1, $R^1$, $R^2$, $R^3$, $R^4$, and $R^5$ individually represent H, F, Cl, methyl, ethyl, methoxy, or ethoxy; and $R^6$ is selected from the group consisting of (morpholinomethyl) amino, (morpholinoethyl)amino, morpholinyl, piperidine, methylpiperidine, dimethylpiperidine, piperazine, methylpiperazine, hydroxymethylpiperazine, hydroxyethylpiperazine, phenylpiperazine, (halophenyl)piperazine, (methoxyphenyl)piperazine, and benzylpiperazine.

6. The pharmaceutical composition according to claim 5, wherein the pyrazolopyrimidine compound represented by the above formula 1 is selected from the group consisting of 1-methyl-6-(4-methylpiperazine-1-yl)-N-phenyl-1H-pyrazolo[3,4-d]pyrimidine-4-amine; $N^6$-(4-chlorophenyl)-1-methyl-6-(4-methylpiperazine-1-yl)-1H-pyrazolo[3,4-d]pyrimidine-4-amine; $N^4$-(4-fluorophenyl)-1-methyl-$N^6$-(2-morpholino ethyl)-1H-pyrazolo[3,4-d]pyrimidine-4,6-diamine; N-(4-fluorophenyl)-1-methyl-6-morpholino-1H-pyrazolo[3,4-d]pyrimidine-4-amine; N-(4-fluorophenyl)-1-methyl-6-(piperidine-1-yl)-1H-pyrazolo[3,4-d]pyrimidine-4-amine; 6-(3,5-dimethylpiperidine-1-yl)-N-(4-fluorophenyl)-1-methyl-1H-pyrazolo[3,4-d]pyrimidine-4-amine; N-(4-fluorophenyl)-1-methyl-6-(4-methylpiperidine-1-yl)-1H-pyrazolo[3,4-d]pyrimidine-4-amine; N-(4-fluorophenyl)-1-methyl-6-(4-methylpiperazine-1-yl)-1H-pyrazolo[3,4-d]pyrimidine-4-amine; 2-(4-(4-(4-fluorophenyl amino)-1-methyl-1H-pyrazolo[3,4-d]pyrimidine-6-yl)piperazine-1-yl)ethanol; 6-(4-benzylpiperazine-1-yl)-N-(4-fluorophenyl)-1-methyl-1H-pyrazolo[3,4-d]pyrimidine-4-amine; N-(4-fluorophenyl)-1-methyl-6-(4-phenylpiperazine-1-yl)-1H-pyrazolo[3,4-d]pyrimidine-4-amine; N-(4-fluorophenyl)-6-(4-(4-fluorophenyl)piperazine-1-yl)-1-methyl-1H-pyrazolo[3,4-d]pyrimidine-4-amine; N-(4-fluorophenyl)-6-(4-(2-methoxyphenyppiperazine-1-yl)-1-methyl-1H-pyrazolo[3,4-d]pyrimidine-4-amine; N-(3-methoxyphenyl)-1-methyl-6-(4-methylpiperazine-1-yl)-1H-pyrazolo[3,4-d]pyrimidine-4-amine; 6-(4-(4-fluorophenyl)piperazine-1-yl)-N-(3-methoxyphenyl)-1-methyl-1H-pyrazolo[3,4-d]pyrimidine-4-amine; 6-(4-(4-fluorophenyl)piperazine-1-yl)-N-(4-methoxyphenyl)-1-methyl-1H-pyrazolo[3,4-d]pyrimidine-4-amine; and N-(4-fluorophenyl)-1-methyl-6-(4-methylpiperazine-1-yl)-1H-pyrazolo[3,4-d]pyrimidine-4-amine.

7. A method of treating a serotonin 5-$HT_{2C}$-related central nervous system disease selected from the group consisting of obesity, depression, anxiety and withdrawal symptoms due to drug abuse which comprises administering an effective amount of a pharmaceutical composition comprising a pyrazolopyrimidine compound or a pharmaceutically acceptable salt of the formula 1 and a pharmaceutically acceptable carrier for the treatment of serotonin 5-$HT_{2C}$-related central nervous system diseases selected from the group consisting of obesity, depression, anxiety and withdrawal symptoms due to drug abuse:

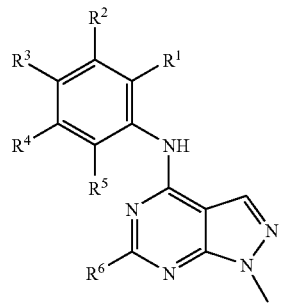

[1]

wherein $R^1$, $R^2$, $R^3$, $R^4$, and $R^5$ independently represent H, halogen, $C_1$-$C_6$ alkyl, $C_1$-$C_6$ alkoxy; and $R^6$ is selected from the group consisting of $C_1$-$C_6$ alkylamino, di($C_1$-$C_6$ alkyl) amino, $C_1$-$C_6$ hydroxyalkylamino, $C_1$-$C_6$ alkoxy$C_1$-$C_6$ alkylamino, $C_2$-$C_6$ alkenylamino, $C_3$-$C_6$ cycloalkylamino, substituted or unsubstituted benzylamino, morpholino $C_1$-$C_6$ alkylamino, morpholinyl, substituted or unsubstituted piperidinyl, substituted or unsubstituted piperazinyl; wherein the above substituted benzyl, piperidinyl, or piperazinyl represents benzyl, piperidinyl, or piperazinyl substituted with 1-3 substituents selected from the group consisting of $C_1$-$C_6$ alkyl, hydroxy $C_1$-$C_6$ alkyl, phenyl, halophenyl, $C_1$-$C_6$ alkoxyphenyl, benzyl, and halobenzyl, to a patient in need thereof.

8. The method of claim 7, wherein in the formula 1, $R^1$, $R^2$, $R^3$, $R^4$, and $R^5$ individually represent H, F, Cl, methyl, ethyl, methoxy, or ethoxy; and $R^6$ is selected from the group consisting of methyl amino, ethyl amino, propylamino, butylamino, cyclopentylamino, cyclohexylamino, dimethyl amino, diethyl amino, (hydroxymethyl)amino, (hydroxyethyl)amino, (hydroxypropyl)amino, (methoxymethyl) amino, (methoxyethyl)amino, (methoxypropyl)amino, (ethoxymethyl)amino, (ethoxyethyl)amino, allylamino, benzylamino, (methylbenzyl)amino, (morpholinomethyl)amino, (morpholinoethyl)amino, morpholinyl, piperidine, methylpiperidine, dimethylpiperidine, piperazine, methylpiperazine, hydroxymethylpiperazine, hydroxyethylpiperazine, phenylpiperazine, (halophenyl)piperazine, (methoxyphenyl)piperazine, and benzylpiperazine.

9. The method according to claim 8, wherein the pyrazolopyrimidine compound is selected from the group consisting of $N^6$-ethyl-1-methyl-$N^4$-phenyl-1H-pyrazolo[3,4-d]pyrimidine-4,6-diamine; 1-methyl-$N^4$-phenyl-$N^6$-propyl-1H-pyrazolo[3,4-d]pyrimidine-4,6-diamine; 1-methyl-6-(4-methylpiperazine-1-yl)-N-phenyl-1H-pyrazolo[3,4-d]pyrimidine-4-amine; $N^4$-(3,4-dimethylphenyl)-$N^6$,$N^6$-diethyl-1-methyl-1H-pyrazolo[3,4-d]pyrimidine-4,6-diamine; $N^4$-(4-chlorophenyl)-$N^6$,$N^6$-diethyl-1-methyl-1H-pyrazolo[3,4-d]pyrimidine-4,6-diamine; $N^6$-(4-chlorophenyl)-1-methyl-6-(4-methylpiperazine-1-yl)-1H-pyrazolo[3,4-d]pyrimidine-4-amine; $N^6$,$N^6$-diethyl-1-methyl-$N^4$-o-tolyl-1H-pyrazolo[3,4-d]pyrimidine-4,6-diamine; $N^4$-(4-fluorophenyl)-$N^6$,1-dimethyl-1-pyrazolo[3,4-d]pyrimidine-4,6-diamine; $N^6$-ethyl-$N^4$-(4-fluorophenyl)-1-methyl-1H-pyrazolo[3,4-d]pyrimidine-4,6-diamine; 3-(4-(4-fluorophenyl amino)-1-methyl-1H-pyrazolo[3,4-d]pyrimidine-6-yl amino)propane-1-ol; $N^4$-(4-fluorophenyl)-$N^6$-(2-methoxyethyl)-1-methyl-1H-pyrazolo[3,4-d]pyrimidine-4,6-diamine; $N^4$-(4-fluorophenyl)-$N^6$-(3-methoxypropyl)-1-methyl-1H-pyrazolo[3,4-d]pyrimidine-4,6-diamine; $N^6$-allyl-$N^4$-(4-fluorophenyl)-1-methyl-1H-pyrazolo[3,4-d]pyrimidine-4,6-diamine; $N^6$-cyclohexyl-$N^4$-(4-fluorophenyl)-1-methyl-1H-pyrazolo[3,4-d]pyrimidine- 4,6-diamine; $N^6$-cyclopentyl-$N^4$-(4-fluorophenyl)-1-methyl-1H-pyrazolo[3,4-d]pyrimidine-4,6-diamine; $N^6$-benzyl-$N^4$-(4-fluorophenyl)-1-methyl-1H-pyrazolo[3,4-d]pyrimidine-4,6-diamine; $N^4$-(4-fluorophenyl)-1-methyl-$N^6$-(4-methylbenzyl)-1H-pyrazolo[3,4-d]pyrimidine-4,6-diamine; $N^4$-(4-fluorophenyl)-1-methyl-$N^6$-(2-morpholinoethyl)-1H-pyrazolo[3,4-d]pyrimidine-4,6-diamine; $N^4$-(4-fluorophenyl)-$N^6$,$N^6$,1-trimethyl-1H-pyrazolo[3,4-d]pyrimidine-4,6-diamine; $N^6$,$N^6$-diethyl-$N^4$-(4-fluorophenyl)-1-methyl-1H-pyrazolo[3,4-d]pyrimidine-4,6-diamine; N-(4-fluorophenyl)-1-methyl-6-morpholino-1H-pyrazolo[3,4-d]pyrimidine-4-amine; N-(4-fluorophenyl)-1-methyl-6-(piperidine-1-yl)-1H-pyrazolo[3,4-d]pyrimidine-4-amine; 6-(3,5-dimethylpiperidine-1-yl)-N-(4-fluorophenyl)-1-methyl-1H-pyrazolo[3,4-d]pyrimidine-4-amine; N-(4-fluorophenyl)-1-methyl-6-(4-methylpiperidine-1-yl)-1H-pyrazolo[3,4-d]pyrimidine-4-amine; N-(4-fluorophenyl)-1-methyl-6-(4-methylpiperazine-1-yl)-1H-pyrazolo[3,4-d]pyrimidine-4-amine; 2-(4-(4-(4-fluorophenyl amino)-1-methyl-1H-pyrazolo[3,4-d]pyrimidine-6-yl)piperazine-1-yl)ethanol; 6-(4-benzylpiperazine-1-yl)-N-(4-fluorophenyl)-1-methyl-1H-pyrazolo[3,4-d]pyrimidine-4-amine; N-(4-fluorophenyl)-1-methyl-6-(4-phenylpiperazine-1-yl)-1H-pyrazolo[3,4-d]pyrimidine-4-amine; N-(4-fluorophenyl)-6-(4-(4-fluorophenyl)piperazine-1-yl)-1-methyl-1H-pyrazolo[3,4-d]pyrimidine-4-amine; N-(4-fluorophenyl)-6-(4-(2-methoxyphenyl)piperazine-1-yl)-1-methyl-1H-pyrazolo[3,4-d]pyrimidine-4-amine; $N^6$,$N^6$-diethyl-$N^4$-(3-methoxyphenyl)-1-methyl-1H-pyrazolo[3,4-d]pyrimidine-4,6-diamine; N-(3-methoxyphenyl)-1-methyl-6-(4-methylpiperazine-1-yl)-1H-pyrazolo[3,4-d]pyrimidine-4-amine; 6-(4-(4-fluorophenyl)piperazine-1-yl)-N-(3-methoxyphenyl)-1-methyl-1H-pyrazolo[3,4-d]pyrimidine-4-amine; 6-(4-(4-fluorophenyl)piperazine-1-yl)-N-(4-methoxyphenyl)-1-methyl-1H-pyrazolo[3,4-d]pyrimidine-4-amine; and N-(4-fluorophenyl)-1-methyl-6-(4-methylpiperazine-1-yl)-1H-pyrazolo[3,4-d]pyrimidine-4-amine.

* * * * *